United States Patent [19]

Agouridas et al.

[11] Patent Number: 5,439,889
[45] Date of Patent: Aug. 8, 1995

[54] ERYTHROMYCIN DERIVATIVES

[75] Inventors: Constantin Agouridas, Nogent sur Marne; Yannick Benedetti, Rosny sous Bois; Jean-Francois Chantot, Gressy en France; Alexis Denis, Paris, all of France

[73] Assignee: Roussel Uclaf, France

[21] Appl. No.: 207,355

[22] Filed: Mar. 7, 1994

[30] Foreign Application Priority Data

Mar. 9, 1993 [FR] France .................. 93 02674

[51] Int. Cl.⁶ .................. C07H 17/08; A61K 31/70
[52] U.S. Cl. .................. 514/29; 514/326; 536/7.2; 536/7.4; 546/207
[58] Field of Search .................. 536/7.2, 7.4; 546/207; 514/326, 29

[56] References Cited

U.S. PATENT DOCUMENTS 4,847,242  7/1989  Davies .................. 514/29

FOREIGN PATENT DOCUMENTS 2534588  4/1984  France .
0284203  9/1988  France .
0487411  5/1992  France .

*Primary Examiner*—Ceila Chang
*Attorney, Agent, or Firm*—Bierman and Muserlian

[57] ABSTRACT

All possible stereoisomeric forms and mixtures thereof of a compound of the formula

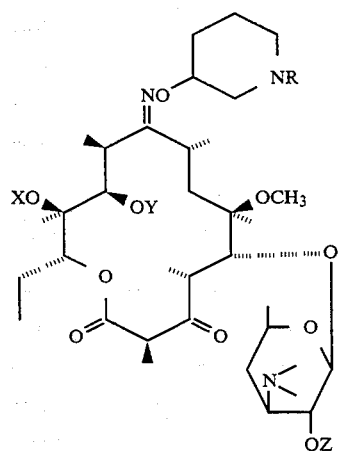

wherein the substituents are as defined in the specification and their non-toxic, pharmaceutically acceptable acid addition salts having antibiotic properties.

10 Claims, No Drawings

ERYTHROMYCIN DERIVATIVES

OBJECTS OF THE INVENTION

It is another object of the invention to provide novel compounds of formula I and their non-toxic, pharmaceutically acceptable acid addition salts and a process for their preparation.

It is another object of the invention to provide novel antibiotic compositions and a novel method of combatting bacterial infections in warm-blooded animals.

These and other objects and advantages of the invention will become obvious from the following detailed description.

THE INVENTION

The novel compounds of the invention are selected from the group consisting of all possible stereoisomeric forms and mixtures thereof of a compound of the formula

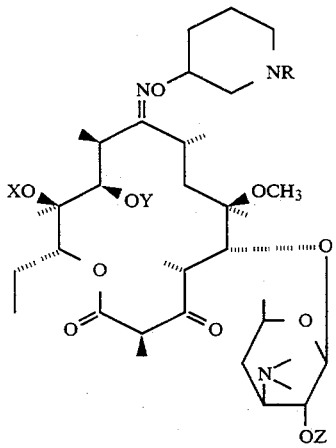

wherein X and Y are hydrogen or together form

R is —(CH$_2$)$_m$—

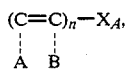

m is an integer from 0 to 20, n is 0, 1, 2 or 3, A and B are individually selected from the group consisting of hydrogen, halogen, alkyl of 1 to 8 carbon atoms and aryl of 6 to 8 carbon atoms with the double bond geometry being E or Z or a mixture of E and Z or A and B form a third bond between the carbons to which they are attached, X$_A$ is selected from the group consisting of alkyl, alkenyl and alkynyl of 6 to 20 carbon atoms optionally interrupted with at least one heteroatom and optionally substituted with at least one halogen, cycloalkyl of 3 to 8 carbon atoms optionally substituted by a carbocyclic aryl, halogen, —CN, —OR$_3$, COR$_4$, —COOR$_5$, —SR$_6$, —SOR$_7$, —SO$_2$R$_8$,

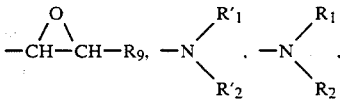

—OC(Ar)$_3$ and a carbocyclic aryl and heterocyclic aryl optionally substituted, R$_3$, R$_4$, R$_5$, R$_6$, R$_7$, R$_8$ and R$_9$ are individually selected from the group consisting of hydrogen, alkyl of 1 to 8 carbon atoms optionally interrupted by at least one heteroatom and optionally substituted by at least one halogen, carbocyclic and heterocyclic aryl and aralkyl of up to 14 carbon atoms optionally substituted with at least one member of the group consisting of free, salified, esterified or amidified carboxy, —OH, halogen, —NO$_2$, —CN, alkyl, alkenyl, alkynyl, alkoxy, alkenyloxy, alkynyloxy, alkylthio, alkenylthio, alkynylthio, —SO-alkyl, —SO-alkenyl, —SO-alkynyl, —SO$_2$— alkyl, —SO$_2$-alkenyl and —S$_2$-alkynyl of up to 12 carbon atoms, all optionally substituted with at least one halogen, carbocyclic and heterocyclic aryl O-aryl and —S-aryl of up to 14 carbon atoms, R'$_1$ and R'$_2$ are individually selected from the group consisting of hydrogen and alkyl of 1 to 12 carbon atoms, R$_1$ and R$_2$ are individually selected from the group consisting of hydrogen, alkyl of 1 to 20 carbon atoms, —COAlk and —COO-Alk, aryl, —CO-aryl, —COO-aryl, aralkyl, —CO-aralkyl and —COO-aralkyl of up to 14 carbon atoms, Alk is alkyl of 1 to 8 carbon atoms, or R$_1$ and R$_2$ together with the nitrogen to which they are attached form ring of 3 to 8 members optionally containing a second heteroatom and optionally substituted with the above aryl substituents, Ar is a carbocyclic aryl optionally substituted with at least one of the above aryl substituents, Z is hydrogen or aryl of an organic carboxylic acid of up to 18 carbon atoms and their non-toxic, pharmaceutically acid addition salts.

The compounds of formula I can exist in all their possible stereoisomeric forms, as well as their mixtures. The oxime in position 9, for example can be of E or Z geometry and includes the E oximes, the Z oximes as well as their E+Z mixtures.

Examples of the acids to form the non-toxic, pharmaceutically acceptable acid addition salts are acetic acid, propionic acid, trifluoroacetic acid, maleic acid, tartaric acid, methane-sulfonic acid, benzene-sulfonic acid, p-toluenesulfonic acid, hydrochloric acid, hydrobromic acid, hydroiodic acid, sulfuric acid, phosphoric acid and stearic acid.

When X$_A$ is alkyl of 6 to 20 carbon atoms, it is preferably hexyl, heptyl, octyl, nonyl, decyl, undecyl, dodecyl, tridecyl, tetradecyl, pentadecyl and hexadecyl, as well as their isomers.

In the definition of the substituents: halogen is preferably fluorine or chlorine or bromine, alkyl, alkenyl or alkynyl are preferably methyl, ethyl, propyl, isopropyl, n-butyl, isobutyl, terbutyl, decyl or dodecyl, vinyl, allyl, ethynyl, propynyl or propargyl. Examples of cycloalkyl are cyclopropyl, cyclobutyl, cyclopentyl or cyclohexyl.

When alkyl is optionally interrupted by one or more heteroatoms, it is preferably one or more oxygen atoms. Carbocyclic aryl is preferably phenyl or naphthyl. By heterocyclic aryl is meant either a monocyclic heteroaryl of 5 or 6 ring members containing one or more heteroatoms, or a condensed polycyclic system, each ring containing 5 or 6 ring members and optionally one or more heteroatoms. Heterocyclic aryl may contain one or more heteroatoms preferably chosen from oxygen, sulfur and nitrogen.

Examples of monocyclic heteroaryl with 5 members are thienyl, furyl, pyrrolyl, thiazolyl, oxazolyl, imidazolyl, thiadiazolyl, pyrazolyl or isoxazolyl. Examples of monocyclic heteroaryl with 6 members are pyridyl, pyrimidinyl, pyridazinyl or pyrazinyl. Examples of condensed polycyclic heteroaryl are indolyl, benzofuryl, benzothienyl or quinolinyl, or the remainder of a purine base such as adenine.

The alkyl, alkenyl or alkynyl are preferably methyl, ethyl, propyl, isopropyl, n-butyl, isobutyl, terbutyl, decyl or dodecyl, vinyl, allyl, ethynyl, propynyl, propargyl, cyclobutyl, cyclopentyl or cyclohexyl and the carboxylic acid remainder is preferably acetyl, propionyl, butyryl, isobutyryl, n-valeryl, iso-valeryl, tert-valeryl or pivalyl.

Among the preferred compounds of the invention are the compounds of formula I in which X and Y are hydrogen, those in which Z is hydrogen, those in which R is

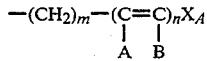

m and n are 0, and $X_A$ is saturated or unsaturated alkyl of 8 to 16 carbon atoms optionally substituted by at least one halogen, or cycloalkyl of 3 to 6 carbon atoms, for example those in which R is undecyl, dodecyl, 3,7,11-trimethyl-2,6,10-dodecatrienyl or 3-cyclohexylpropyl, as well as their addition salts with acids.

Other preferred compounds of formula I are those wherein R is

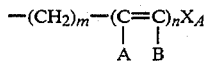

in which $X_A$ is phenyl optionally substituted by one of the radicals mentioned above as substituents of the aryl radicals, m, n, A and B are as defined above and preferably n is 0 or 1, or is an integer of 2 to 6 and those in which $X_A$ is phenyl optionally substituted by at least one member of the group consisting of halogen, methyl, trifluoromethyl, hydroxy, methoxy, phenyl or phenoxy optionally substituted by at least one halogen.

Also preferred are the compounds in which R is —(CH$_2$)$_3$Ar, —(CH$_2$)$_4$—Ar or —CH$_2$—CH=CH—Ar, Ar is optionally substituted phenyl, as well as their addition salts with acids and those wherein $X_A$ is

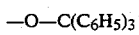

in which phenyl is optionally substituted by at least one of the substituents indicated above as well as their addition salts with acids.

Among the compounds of the invention, there can also be mentioned the compounds of formula I wherein $X_A$ is

in which $R_1$ and $R_2$ are individually hydrogen or alkyl of up to 12 carbon atoms and particularly dodecylamino.

A more particular subject of the invention are the compounds of Examples 1, 2, 4, 5, 21, 25, 26, 33, 37, 38, 42, 48, 51, 54, 57, 64, 65 and 66.

The novel antibiotic components of the invention are comprised of an antibiotically effective amount of at least one compound of formula I and their non-toxic, pharmaceutically acceptable acid addition salts and an inert pharmaceutical carrier. The compositions may be in the form of tablets, dragees, capsules, granules, suppositories, ointments, creams, gels, and injectable solutions or suspension.

Examples of suitable inert pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives. The compositions can also be in the form of a powder intended to be dissolved extemporaneously in an appropriate vehicle, for example apyrogenic sterile water.

The compositions have a very good antibiotic activity on gram positive bacteria such as staphylococci, streptococci and pneumococci and therefore can be used for the treatment of infections caused by sensitive germs and, particularly, staphylococcia such as staphylococcal septicemias, malignant staphylococcia of the face or skin, pyodermatitis, septic or suppurating wounds, boils, anthrax, phlegmons, erysipelas and acne, staphylococcia such as acute primary or post-influenzal angina, bronchopneumonia, pulmonary suppuration, streptococcia such as acute anginas, otitis, sinusitis, scarlet fever, pneumococcia such as pneumonia, bronchitis; brucellosis, diptheria, gonococcal infection. The compositions are also active against infections caused by germs such as *Haemophilus influenzae*, Rickettsies, *Mycoplasma pneumoniae*, Chlamydia, Legionella, Ureaplasma, Toxoplasma, Listeria, Campylobacter and Meningococcus.

The novel method of the invention for combatting bacterial infections in warm-blooded animals comprising administering to warmblooded animals an anti-bacterially effective amount of at least one compound of formula I and their non-toxic, pharmaceutically acceptable acid addition salts. The compounds may be administered rectally, orally or parenterally as well as topically to the skin or mucous membrane. The usual useful daily dose is 0.70 to 4 mg/kg depending on the condition treated, the compound used and the method of administration.

The process for the preparation of the compounds of formula I comprises reacting all possible stereoisomers and mixtures thereof of a compound of the formula

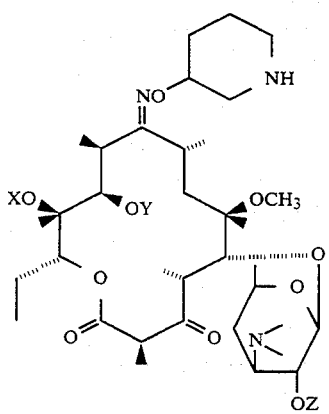

wherein X, Y and Z have the above definitions with a compound of the formula

RCHO     III wherein R has the above definition to obtain the corresponding compound of formula I which is optionally reacted with an esterification agent to esterify the 2'-hydroxyl or with an acid to form the acid addition salt.

Preferably, the compounds of formulae II and III are reacted in the presence of NaBH$_3$CN or in the presence of hydrogen and a suitable catalyst such as palladium on activated charcoal. The optional esterification of the 2'-hydroxyl may be effected with known procedures and the salification may be effected with the appropriate acid.

The compounds of formula II in all their stereoisomeric forms as well as their mixtures are described in European Patent Application 0487411. The compounds of formula II in which the 9-oxime is of E geometry can be obtained by chromatography starting with R+S diastereosiomer mixtures at the level of the 3-carbon of the piperidine, or can be obtained by using chiral (S) 3-hydroxy piperidine obtained by resolution using as active ingredient a chiral acid by the process described in European Patent Application 487411 (cf preparation of Example 27).

The compounds of formula III are known in a general manner and can be prepared by the reaction scheme

using standard processes.

In the following examples, there are described several preferred embodiments to illustrate the invention. However, it is to be understood that the invention is not intended to be limited to the specific embodiments.

The compounds prepared hereafter are prepared according to one of the following 3 general operating methods: In what follows, 3-de [(2,6-dideoxy-3-C-methyl-3-O-methyl-α-L-ribohexopyranosyl)-oxy]-6-O-methyl-3-oxo-erythromycin (R) (E) 9-O-(3-piperidinyl)oxime is called Product A.

Operating method 1

0.5 mM of product A, 0.5 mM of aldehyde were dissolved in 4 ml of methanol or 3 ml of methyl cyanide+1 ml of methanol and 0.1 ml of glacial acetic acid was added thereto. The mixture was stirred for 5 to 10 minutes and 0.55 mM of NaBH$_3$CN were added all at once. The mixture was stirred at ambient temperature for 15 to 60 minutes and then the solution was concentrated under reduced pressure. After taking the residue up in 10 ml of water and 30 ml of ethyl acetate, the pH was adjusted to about 8 with sodium hydroxide, followed by decanting, extracting, washing the aqueous phase with 10 ml of ethyl acetate, then washing the organic phases with a saturated solution of sodium chloride. After drying over magnesium sulfate, the product was purified by chromatographing on silica, eluting with mixtures of the following type: ethyl acetate-triethylamine; isopropyl ether-triethylamine-methanol; methylene chloride-methanol; methylene chloride-methanol-ammonium hydroxide; chloroform-methanol-ammonium hydroxide; ethyl acetate-methanol; ethyl acetate-methanol-triethylamine to obtain the desired product.

Operating method 2

0.4 mM of product A, 0.45 mM of aldehyde were dissolved in 10 ml of methanol and 30 μl of glacial acetic acid and 50 mg of palladium on activated charcoal were added. The mixture was stirred under 1.5 atmospheres of hydrogen for 2 to 24 hours. The solution was filtered on clarcel, rinsed with 20 ml of methanol and the solution was concentrated. Purification was carried out by chromatographing on silica, eluting with one of the eluant systems in operating method 1 to obtain the desired product.

Operating method 3

0.2 mM of product A and 0.3 mM of aldehyde were dissolved in 0.6 ml of methyl cyanide and 0.5 ml of a solution of sodium acid phosphate and the mixture was stirred for 5 minutes. Then, 30 mg (0.48 mM) of NaBH$_3$CN were added and the pH was adjusted to approx. 4.5 by adding a hydrochloric acid solution dropwise. The reaction was completed in 5 to 60 minutes and 5 ml of water were added. The pH was adjusted to 8 with sodium hydroxide and extraction was carried out with 2×10 ml of chloroform. The organic phases were dried over magnesium sulfate and purification was carried out by chromatographing on silica using one of the eluant systems in operating method 1 to obtain the desired product.

EXAMPLE 1

3-de[(2,6-dideoxy-3-C-methyl-3-O-methyl-α-L-ribohexopyranosyl)oxy]-6-O-methyl-3-oxo-erythromycin (R) (E) 9-O-(1-(3-phenylpropyl)-3-piperidinyl)-oxime was obtained using Operating Method 1 and its Mass spectrum: MH+ =804+ NMR CDCl$_3$ ppm 2.25–2.75–2.98 (m) CH$_2$N; 2.26 (s) NCH$_3$; 2.74 (s) 6-OCH$_3$; 3.69 (m) H$_8$; 3.86 (q) H$_2$; 4.04 (m) NOCH; 5.17 (dd) H$_{13}$; 7.1 to 7.3 aromatics.

EXAMPLE 2

3-de[(2,6-dideoxy-3-C-methyl-3-O-methyl-α-L-ribohexopyranosyl)-oxy]-6-O-methyl 3-oxo-erythromycin (R)(E) 9-O-( 1-dodecyl-3-piperidinyl)-oxime was obtained using Operating Method 2 and its Mass spectrum: MH+ =854+ NMR CDCl$_3$ ppm 126 the (CH$_2$)$_n$'s; 2.15 2.4–2.7–2.98 (m) CH$_2$N; 2.26 (s) NCH$_3$; 2.74 (s) 6-OCH$_3$; 3.68 (m) H$_8$; 3.87 (q) H$_2$; 4.04 (m) NOCH; 5.17 (dd) H$_{13}$.

EXAMPLE 3

3-de[(2,6-dideoxy-3-C-methyl-3-O-methyl-α-L-ribohexopyranosyl)-oxy]-6-O-methyl-3-oxo-erythromycin (R) (E)9-O-(1-octyl-3-piperidinyl)-oxime was obtained using Operating Method 1 and its Mass spectrum:

MH+ =798+ NMR CDCl3 ppm 1.22 to 1.33 (CH2)$_n$ and 12CH3; 2.26 (s) NCH3; 2.74 (s) 6-OCH3; 2.2–2.7–2.98 the CH2N's; 3.68 (m) H8; 3.86 (q) H2; 4.04 (m) NOCH; 5.17 (dd) H13.

EXAMPLE 4

3-de[(2,6-dideoxy-3-C-methyl-3-O-methyl-α-L-ribohexopyranosyl)-oxo]-6-O-methyl-3-oxo-erythromycin (R) (E)9-O-(1-(3-(3-methoxyphenyl)-propyl)-3-piperidinyl)-oxime was obtained using Operating Method 2 and its Mass spectrum: MH+ =834+ NMR CDCl3 ppm 1.23 (s) 12CH3; 2.26 (s) NCH3; 2.74 (s) 6-OCH3; 2.3 to 2.6 the CH2N's; 3.68 (m) H8; 3.80 (s) ΦOCH3; 3.87 (q) H2; 4.04 (m) NOCH; 5.17 (dd) H13; 6.69–6.87–7.19 the aromatics.

EXAMPLE 5

3-de[(2,6-dideoxy-3-C-methyl-6-O-methyl-α-L-ribohexopyranosyl)-oxy]-6-O-methyl-3-oxo-erythromycin (R) (E) 9-O-(1-(4-triphenylmethoxy)-butyl)-3-piperidinyl)-oxime was obtained using Operating Method 1 and its Mass spectrum: MH+ =1000+ NMR CDCl3 ppm 1.23 (s) 12CH3; 2.26 (s) NCH3; 2.1 to 2.4–2.97–2.72 the CH2N's; 3.06 CH2O; 3.66 (m) H8; 3.86 (q) H2; 5.17 (dd) H13; 7.17 to 7.30–7.44 (m) the aromatics.

EXAMPLE 6

3-de[(2,6-dideoxy-3-C-methyl-3-O-methyl-α-L-ribohexopyranosyl)-oxo]-6-O-methyl-3-oxo-erythromycin (R) (E) 9-O-(1-(4-hydroxybutyl)-3-piperidinyl)-oxime was obtained using Operating Method 1 and its Mass spectrum: MH+ =758+ NMR CDCl3 ppm 1.23 (s) 12CH3; 2.26 (s) NCH3; 2.38 (sl) NCH2 2.74 (s) 6-OCH3; 3.56 (sl) CH2OH; 3.70 (m) H8; 3.86 (q) H2; 4.08 (m) NOCH.

EXAMPLE 7

3-de[(2,6-dideoxy-3-C-methyl-3-O-methyl-α-L-ribohexopyranosyl)-oxo]-6-O-methyl-3-oxo-erythromycin (R) (E) 9-O-(1-(2-aminoethyl)-3-piperidinyl)-oxime was obtained using Operating Method 1 and its Mass spectrum: MH+ =729+ NMR CDCl3 ppm 1.23 (s) 12CH3; 2.26 (s) NCH3; 2.4 (m)-2.76 (m) the CH2N's; 3.68 (m) H8; 3.86 (q) H2; 4.04 (m) NOCH; 5.17 (dd) H13.

EXAMPLE 8

3-de[(2,6-dideoxy-3-C-methyl-3-O-methyl-α-L-ribohexopyranosyl)-oxo]-6-O-methyl-3-oxo-erythromycin (R) (E) 9-O-(1-(3-(3-trifluoromethyl-phenyl)-oxy)-benzyl)-3-piperidinyl)-oxime was obtained using Operating Method 1 and its Mass spectrum: MH+ =936+ NMR CDCl3 ppm 2.70 6-OMe; 3.86 (q,J=6 Hz) H2; 3.67 (E) H8; 2.27 N(CH3)2; 3.40 (d,J=14 )-3.459 (d,J=14) N—CH2—Φ.

EXAMPLE 9

3-de[(2,6-dideoxy-3-C-methyl-3-O-methyl-α-L-ribohexopyranosyl)-oxo]-6-O-methyl-3-oxo-erythromycin (R) (E) 9-O-(1-(2-phenethyl)-3-piperidinyl)-oxime was obtained using Operating Method 1 and its Mass spectrum: MH+ =790+ NMR CDCl3 ppm 2.74 6-OMe; 3.86 H2; 3.70 (E) H8; 7.15 to 7.35 Φ-; 2.5 to 2.7–2.77–3.04 N—CH2—CH2—Φ and CH2N.

EXAMPLE 10

3-de[(2,6-dideoxy-3-C-methyl-3-O-methyl-α-L-ribohexopyranosyl)-oxo]-6-O-methyl-3-oxo-erythromycin (R) (E) 9-O-(1-(4-(4-methoxyphenyl)-butyl)-3-piperidinyl)-oxime was obtained using Operating Method 2 and its Mass spectrum: MH+ =848+ NMR CDCl3 ppm 2.26 N(CH3) 2; 2.74 (s) 6-OMe; 3.68 H8; 3.79 Φ-OMe; 2.25 to 2.75–2.96 CH2N and CH2Φ; 3.87 H2.

EXAMPLE 11

3-de[(2,6-dideoxy-3-C-methyl-3-O-methyl-α-L-ribohexopyranosyl)-oxy)-6-O-methyl-3-oxo-erythromycin (R) (E) 9-O-(1-(3-(1-(benzyl)-1H-indol-4-yl)-propyl-3-piperidinyl)-oxime was obtained using Operating Method 1 and its Mass spectrum: MH+ =933+ NMR CDCl3 ppm 2.26 N(CH3)2; 2.74 6-OMe; 2.91 CH2—Φ; 3.68 H8; 3.86 H2; 4.06 axial N—O—CH: 5.32 NCH2Φ; 6.58–6.92–7.05 to 7.30 the aromatics.

EXAMPLE 12

3-de[(2,6-dideoxy-3-C-methyl-3-O-methyl-α-L-ribohexopyranosyl)-oxy]-6-O-methyl-3-oxo-erythromycin (R) (E) 9-O-(1-(3-imidazolylpropyl)-3-piperidinyl)-oxime was obtained using Operating Method 1 and its Mass spectrum: MH+ =794+ NMR CDCl3 ppm 2.26 N(Me)2; 2.74 6-OMe; 3.18 H2'; 3.68 H8; 3.89 H2; 4.00 CH2—N—C≡; 4.05 N—O—CH; 7.46–6.92–7.05 imidazole.

EXAMPLE 13

3-de[(2,6-dideoxy-3-C-methyl-3-O-methyl-α-L-ribohexopyranosyl)oxy]-6-O-methyl-3-oxo-erythromycin (R) (E) 9-O-(1-(4-phenylbutyl)-3-piperidinyl)-oxime was obtained using Operating Method 1 and its Mass spectrum: MH+ =818+ NMR CDCl3 ppm 2.26 N(Me)2; 2.62 CH2—Φ; 2.73 6-OMe; 3.19 H2'; 3.68 H8; 3.89 H2; 4.03 N—O—CH: 7.18–7.21 Aromatics.

EXAMPLE 14

3-de[(2,6-dideoxy-3-C-methyl-3-O-methyl-α-L-ribohexopyranosyl)-oxy]-6-O-methyl-3-oxo-erythromycin (R) (E) 9-O-(1-(((1,1'-biphenyl)-4-yl)-methyl)-3-piperidinyl)-oxime was obtained using Operating Method 1 and its Mass spectrum: MH+ =852+ NMR CDCl3 ppm 2.73 (s) 6-OMe; 3.69 (m) H8; 3.86 (q) H2; 3.47–3.63 (d) N—CH2—Φ; 4.09 (m) axial NO—CH.

EXAMPLE 15

3-de[(2,6-dideoxy-3-C-methyl-3-O-methyl-α-L-ribohexopyranosyl)-oxy]-6-O-methyl-3-oxo-erythromycin (R) (E) 9-O-(1-(pentafluorobenzyl)-3-piperidinyl)-oxime was obtained using Operating Method 1 and its Mass spectrum: MH+ =866+ NMR CDCl3 ppm 6-OMe; 3.5 to 3.75 H8; 3.86 (q) H2; ~3.72 N—CH2—Φ; 4.03 (m) axial NO—CH.

EXAMPLE 16

3-de[(2,6-dideoxy-3-C-methyl-3-O-methyl-α-L-ribohexopyranosyl)-oxy]-6-O-methyl-3-oxo-erythromycin (R) (E) 9-O-(1-((3-cyano-benzyl)-3-piperidinyl)-oxime was obtained using Operating Method 3 and its Mass spectrum: MH+ =800+ NMR CDCl3 ppm 2.68 (s) 6-OMe; 3.6 H8; 3.87 (q) H2; 3.43 (d) 3.60 N—CH2—Φ; 4.07 (m) axial NO—CH.

EXAMPLE 17

3-de[(2,6-dideoxy-3-C-methyl-3-O-methyl-α-L-ribohexopyranosyl)-oxy]-6-O-methyl-3-oxo-erythromycin (R) (E) 9-O-(1-((1H-imidazol-2-yl)-methyl)-3-piperidinyl)-oxime was obtained using Operating Method 1 and its Mass spectrum: MH+ =766+ NMR CDCl₃ ppm 2.66 (s) 6-OMe; 3.5 to 3.7 H₈; 3.87 (q) H₂; 4.09 (m) NO—CH.

EXAMPLE 18

3-de[(2,6-dideoxy-3-C-methyl-α-L-ribohexopyranosyl)-oxy]-6-O-methyl-3-oxo-erythromycin (R) (E) 9-O-(1-((3-methyl-2-thienyl)-methyl)-3-piperidinyl)-oxime was obtained using Operating Method 1 and its Mass spectrum: MH⁺=796+ NMR CDCl₃ ppm 2.70 (s) 6-OMe; 3.5 to 3.75 H₈; 3.86 (q) H₂; 4.06 (m) axial NO—CH; 6.77 (d) 7.11 (d) H₄ H₅ thiophene.

EXAMPLE 19

3-de[(2,6-dideoxy-3-C-methyl-3-O-methyl-α-L-ribohexopyranosyl)-oxy]-6-O-methyl-3-oxo-erythromycin (R) (E) 9-O-(1-(3,3-dimethylbutyl)-3-piperidinyl)-oxime was obtained using Operating Method 2 and its Mass spectrum: MH⁺=770+ NMR CDCl₃ ppm 2.74 (s) 6-OMe; 3.69 (m) H₈; 3.86 (q) H₂; 4.04 (m) NO—CH.

EXAMPLE 20

3-de[(2,6-dideoxy-3-C-methyl-3-O-methyl-α-L-ribohexopyranosyl)-oxy]-6-O-methyl-3-oxo-erythromycin (R) (E) 9-O-(1-(3-(methylthio)-propyl)-3-piperidinyl)-oxime was obtained using Operating Method 2 and its Mass spectrum: MH⁺=774+ NMR CDCl₃ ppm 2.74 (s) 6-OMe; 3.67 (m) H₈; 3.86 (q) H₂; 4.04 (m) axial NO—CH.

EXAMPLE 21

3-de[(2,6-dideoxy-3-C-methyl-3-O-methyl-α-L-ribohexopyranosyl)-oxy]-6-O-methyl-3-oxo-erythromycin trans (R) (E) 9-O-(1-(3-phenyl-2-propenyl)-3-piperidinyl)-oxime was obtained using Operating Method 1 and its Mass spectrum: MH⁺=802+ NMR CDCl₃ ppm 2.74 (s) 6-OMe; 3.68 (m) H₈; 3.86 (q) H₂; 4.07 (m) axial NO—CH; 6.24 (dt, J=15.5 and 7) 6.49 (d, J=15.5 ethylenic ΔE).

EXAMPLE 22

3-de[(2,6-dideoxy-3-C-methyl-3-O-methyl-α-L-ribohexopyranosyl)-oxy]-6-O-methyl-3-oxo-erythromycin (R) (E) 9-O-(1-(2-methoxy-benzyl)-3-piperidinyl)-oxime was obtained using Operating Method 1 and its Mass spectrum: MH⁺=806+ NMR CDCl₃ ppm 2.68 (s) 6-OMe; 3.5 to 3.75 H₈; 3.86 (q) H₂; 4.07 (m) axial NO—CH.

EXAMPLE 23

3-de[(2,6-dideoxy-3-C-methyl-3-O-methyl-α-L-ribohexopyranosyl)-oxy]-6-O-methyl-3-oxo-erythromycin (R) (E) 9-O-(1-decyl-3-piperidinyl)-oxime was obtained using Operating Method 2 and its Mass spectrum: MH⁺=826+ NMR CDCl₃ ppm 2.74 (s) 6-OMe; 3.68 (m) H₈; 3.86 (q) H₂; 4.04 (m) axial NO—CH.

EXAMPLE 24

3-de[(2,6-dideoxy-3-C-methyl-3-O-methyl-α-L-ribohexopyranosyl)-oxy]-6-O-methyl-3-oxo-erythromycin (R) (E) 9-O-(1-(9-ethoxy 9-oxo-nonyl)-3-piperidinyl)-oxime was obtained using Operating Method 2 and its Mass spectrum: MH⁺=870+ NMR CDCl₃ ppm 2.74 (s) 6-OMe; 3.68 (m) H₈; 3.86 (q) H₂; 4.03 axial NO—CH.

EXAMPLE 25

3-de[(2,6-dideoxy-3-C-methyl-3-O-methyl-α-L-ribohexopyranosyl)-oxy]-6-O-methyl-3-oxo-erythromycin (R) (E) 9-O-(1-(3-(4-(trifluoromethyl)-phenyl)-propyl)-3-piperidinyl)-oxime was obtained using Operating Method 2 and its Mass spectrum: MH⁺=872+ NMR CDCl₃ ppm 1.23 (s) 12CH₃; 2.26 (s) NCH₃; 2.67 CH₂Φ; 2.74 (s) 6-OCH₃; 3.67 (m) H₈; 3.87 (q) H₂; 4.04 (m) NO—CH; 5.17 (dd) H₁₃; 7.30–7.53 the aromatics.

EXAMPLE 26

3-de[(2,6-dideoxy-3-C-methyl-3-O-methyl-α-L-ribohexopyranosyl)-oxy]-6-O-methyl-3-oxo-erythromycin (R) (E) 9-O-(1-(3-(3,4-difluorophenyl)-propyl)-3-pyridinyl)-oxime was obtained using Operating Method 2 and its Mass spectrum: MH⁺=840+ NMR CDCl₃ ppm 1.23 (s) 12CH₃; 2.28 (s) NCH₃; 2.58 CH₂Φ; 2.74 (s) 6-OCH₃; 3.68 (m) H₈; 3.87 (q) H₂; 4.04 (m) NO—CH; 5.17 (dd) H₁₃; 6.95–7.10 the aromatics.

EXAMPLE 27

3-de[(2,6-dideoxy-3-C-methyl-3-O-methyl-α-L-ribohexopyranosyl)-oxy]-6-O-methyl-3-oxo-erythromycin (R) (E) 9-O-(1-(2-phenoxyethyl)-3-piperidinyl)-oxime was obtained using Operating Method 1 and its Mass spectrum: MH⁺=806+ NMR CDCl₃ ppm 1.22 (s) 12CH₃; 2.26 (s) NCH₃; 2.74 (s) 6-OCH₃; 3.68 (m) H₈; 3.86 (q) H₂; 4.04 (m) NO—CH; 4.08 (t) CH₂OΦ; 5.17 (dd) H₁₃; 6.85–7.25 the aromatics.

EXAMPLE 28

3-de[(2,6-dideoxy-3-C-methyl-3-O-methyl-α-L-ribohexopyranosyl)-oxy] -6-O-methyl-3-oxo-erythromycin (R) (E) 9-O-(1-(2-((benzyl-amino)-ethyl)-3-piperidinyl)-oxime was obtained using Operating Method 1 and its Mass spectrum: MH⁺=819+ NMR CDCl₃ ppm 1.23 (S) 12CH₃; 2.26 (s) NCH₃; 2.73 (s) 6-OCH₃; 3.66 (m) 3.80 (s) NCH₂Φ; 4.01 (m) NO—CH; 5.17 (dd) H₁₃; 7.27–7.32 (m) the aromatics.

EXAMPLE 29

3-de[(2,6-dideoxy-3-C-methyl-3-O-methyl-α-L-ribohexopyranosyl)-oxy] (E) (R) 9-O-(1-(2-(methyl-benzyl-amino)-ethyl)-3-piperidinyl)oxime was obtained using Operating Method 1 and its Mass spectrum: MH⁺=833+ NMR CDCl₃ ppm 1.22 (s) 12CH₃; 2.22 (s) NCH₃; 2.26 (s) NCH₃ desosamine; 2.76 (s) 6-OCH₃; 3.51 (s) NCH₂Φ; 3.68 (m) H₈; 3.87 (q) H₂; 4.03 (m) NO—CH; 7.20 to 7.40 aromatics.

EXAMPLE 30

3-de((2,6-dideoxy-3-C-methyl-3-O-methyl-α-L-ribohexopyranosyl)-oxy]-6-O-methyl-3-oxo-erythromycin (R) (E) 9-O-(1-(3-(4-methoxyphenyl)-propyl)-3-piperidinyl)-oxime was obtained using Operating method 1 and its Mass spectrum: MH⁺=834+ NMR CDCl₃ ppm 1.23 (s) 12CH₃; 2.26 (s) NCH₃; 2.55 (m) CH₂Φ; 2.74 (s) 6-OCH₃; 3.67 (m) H₈; 3,79 (s) ΦOCH₃; 3.86 (q) H₂; 4.04 (m) NO—CH; 5.18 (dd) H₁₃; 6.82–7.10 the aromatics,

EXAMPLE 31

3-de((2,6-dideoxy-3-C-methyl-3-O-methyl-α-L-riboxhexopyranosyl)-oxy]-6-O-methyl-3-oxo-erythromycin (R) (E) 9-O-(1-(2-((benzyl-((phenylmethoxy)-carbonyl)-amino)-ethyl)-3-piperidinyl)-oxime was obtained using Operating Method 1 and its Mass spectrum: MH⁺=953+ NMR CDCl₃ ppm 1.23 (s) 12Me; 2.26 (s) NCH₃; 2.71 (s) 6-OCH₃; 2.92–3.30–3.37 (m) NCH₂; 3,68

(m) H$_8$; 3.87 (q) H$_2$; 3.98 (m) NO<u>CH</u>; 4.55 N<u>CH$_2$</u>—Φ; 7.2 to 7,40 the aromatics.

EXAMPLE 32

3-de[(2,6-dideoxy-3-C-methyl-3-O-methyl-α-L-ribohexopyranosyl)-oxy]-6-O-methyl-3-oxo-erythromycin (E) (R) 9-O-(1-((2-benzofuranyl)-methyl)-3-piperidinyl)-oxime was obtained using Operating Method 1 and its Mass spectrum: MH$^+$ =816$^+$ NMR CDCl$_3$ ppm 1.22: 12Me; 1.35: 6Me; 2.27: N-(Me)$_2$; 2.56: H$_{10}$; 2.74: 6-OMe; 3.19: H$_2'$; 3,65: H$_8$; 3.87: H$_2$; 4.11: NO—CH; 6.56: benzofuran H$_3$.

EXAMPLE 33

3-de[(2,6-dideoxy-3-C-methyl-3-O-methyl-α-L-ribohexopyranosyl)-oxy]-6-O-methyl-3-oxo-erythromycin-(E) (Z) 9-O-(1-(4-(4-methylphenyl)butyl)-3-piperidinyl)-oxime was obtained using Operating Method 1 and its Mass spectrum: MH$^+$ =832$^+$ NMR CDCl$_3$ ppm 1.23: 12Me; 1.37: 6Me; 2.26: N-(Me)$_2$; 2.57:H$_{10}$ and CH$_2$Φ; 2.73: 6-OMe; 3.19: H$_2'$; 3.68: H$_8$; 3.86: H$_2$; 4.03: NO—CH; 7.07: - - - .

EXAMPLE 34

3-de[(2,6-dideoxy-3-C-methyl-3-O-methyl-α-L-ribohexopyranosy)-oxy]-6-O-methyl-3-oxo-erythromycin (E) (R) 9 -O-(1-hexadecyl)-3-piperidinyl)-oxime was obtained using Operating Method 2 and its Mass spectrum: MH$^+$ =910$^+$ NMR CDCl$_3$ ppm 1.7–1.33: 12Me; 1.38: 6Me; 2.26: N-(Me)$_2$; 2.56: H$_{10}$; 2.74: 6-OMe; 3.19: H$_2'$; 3.68: H$_8$; 3.86: H$_2$; 4.04: NO—CH.

EXAMPLE 35

3-de[(2,6-dideoxy-3-C-methyl-3-O-methyl-α-L-ribohexopyranosyl)-oxy]-6-O-methyl-3-oxo-erythromycin (E) (R) 9-O-(1-(2-(1-oxononylamino)-ethyl)-3-piperidinyl)-oxime was obtained using Operating Method 1 and its NMR CDCl$_3$ ppm 1.32 (s): 6Me; 2.17 (t): CH$_2$—CO; 2.26 (s): N(Me)$_2$; 3.32 (m): CH$_2$NCO; 3.67 (m): H$_8$; 3.86 (q): H$_2$; 4.02 (m): NO—CH; 5.17 (dd): H$_{13}$.

EXAMPLE 36

3-[(2,6-dideoxy-3-C-methyl-3-O-methyl-α-L-ribohexopyranosyl)-oxy]-6-O-methyl-3-oxo-erythromycin trans (E) (R) 9-O-(1-((2-phenyl-l-cyclopropyl)-methyl)-3-piperidinyl)-oxime was obtained using Operating Method 1 and its Mass spectrum: MH$^+$ =816$^+$ NMR CDCl$_3$ ppm 1.22 (s): 12Me; 1.35 (s): 6Me; 2.26 (s): N-(Me)$_2$; 3.67: 3.86 (q): H$_2$; 4.05: NO—CH; 5.17 (dd): H$_{13}$; 7.04–7.23: aromatics.

EXAMPLE 37

3-de[(2,6-dideoxy-3-C-methyl-3-O-methyl-α-L-ribohexopyranosyl)-oxy]-6-O-methyl-3-oxo-erythromycin (E) (R) 9-O-(1-(3-cyclohexylpropyl)-3-piperidinyl)-oxime was obtained using Operating Method 1 and its Mass spectrum: MH$^+$ =810$^+$ NMR CDCl$_3$ ppm 1.23: 12Me; 1.37: 6Me; 2.28: N-(Me)$_2$; 2.57: H$_{10}$; 2.73: 6-OMe; 3.20: H$_2'$; 3.68: H$_8$; 3.86: H$_2$; 4.13: N—OCH.

EXAMPLE 38

3-de[(2,6-dideoxy-3-C-methyl-3-O-methyl-α-L-ribohexopyranosyl)-oxy]-6-O-methyl-3-oxo-erythromycin (E) (R) 9-O-(1-(3-(4-hydroxyphenyl)-propyl)-3-piperidinyl)-oxime was obtained using Operating Method 1 and its NMR CDCl$_3$ ppm 1.23: 12Me; 1.34: 6Me; 2.28: N-(Me)$_2$; 2.75: H$_{10}$; CH$_2$Φ: 2.25 to 2.65; 2.66: 6-OMe; 3.19: H$_2'$; 3.65: H$_8$; 3.88: H$_2$; 4.07: NO—CH; 6.75–6.79: —Φ-O; 3.33–4.37: OH.

EXAMPLE 39

3-de[(2,6-dideoxy-3-C-methyl-3-O-methyl-α-L-ribohexopyranosyl)-oxy]-6-O-methyl-3-oxo-erythromycin (E) (R) 9-O-( 1-(3-(((phenylmethoxy)-carbonyl)-benzyl)-amino)-propyl)3-piperidinyl)-oxime was obtained using Operating Method 1 and its Mass spectrum: MH$^+$ =967.9$^+$ NMR CDCl$_3$ ppm 1.22 (s): 12Me; 1.37 (s): 6Me; 2.26 (s): N-(Me)$_2$; 2.72 (s): 6-OMe; 3.66 (m) : H$_8$; 3.85 (q) : H$_2$; 4.5: NCH$_2$Ar; 5.16: OCH$_2$Ar; 7.14 to 7.4: aromatics.

EXAMPLE 40

3-de[(2,6-dideoxy-3-C-methyl-3-O-methyl-α-L-ribohexopyranosyl)-oxy]-6-O-methyl-3-oxo-erythromycin (E) (R) 9-O-(1-(3,3-diphenyl-2-propenyl)-3-piperidinyl)-oxime was obtained using Operating Method 1 and it Mass spectrum: MH$^+$=877$^+$ NMR CDCl$_3$ ppm 1.22 (s): 12Me; 1.36 (s): 6Me; 2.26 (s): N-(Me)$_2$; 2.70 (s): 6-OCH$_3$; 3.66 (m): H$_8$; 3.85 (q): H$_2$; 4.04 (m): NO—CH; 6.17 (t)=CH; 7.10 to 7.4: aromatics.

EXAMPLE 41

3-de[(2,6-dideoxy-3-C-methyl-3-O-methyl-α-L-ribohexopyranosyl)-oxy]-6-O-methyl-3-oxo-erythromycin (E) (R) 9-O-(1-(3-(4-chlorophenyl)-2 (E)-propenyl)-3-piperidinyl)-oxime was obtained using Operating Method 1 and its Mass spectrum: MH$^+$ =836$^+$ NMR CDCl$_3$ppm 1.22 (s): 12Me; 1.38 (s): 6Me; 2.26 (s): N-(Me)$_2$; 2.74 (s): 6-OMe; 3.68 (m): H$_8$; 4.06 (m): NO—CH; 5.14 (dd): H$_{13}$; 6.2 (dt) and 6.43 (d): ethylenics; 7.2–7.3: aromatics.

EXAMPLE 42

3-de[(2,6-dideoxy-3-C-methyl-3-O-methyl-α-L-ribohexopyranosyl)-oxy]-6-O-methyl-3 -oxo-erythromycin (E) (R) 9-O-(1-undecyl-3-piperidinyl)-oxime was obtained using Operating Method 1 and its Mass spectrum: MH$^+$ =840$^+$ NMR CDCl$_3$ ppm 1.26 (m): CH$_2$n and 12Me; 1.38 (s): 6Me; 2.26 (s): N-(Me)$_2$; 2.56: H$_{10}$; 2.74 (s): 6-OMe; 3.68 (m): H$_8$; 3.86 (q): H$_2$; 4.03 (m): NO—CH; 5.17 (dd): H$_{13}$.

EXAMPLE 43

3-de[(2,6-dideoxy-3-C-methyl-3-O-methyl-α-L-ribohexopyranosyl)-oxy]-6-O-methyl-3-oxo-erythromycin (E) (R) 9 -O-(1-3-benzyl-amino)-propyl)-3-piperidinyl)-oxime was obtained using Operating Method and its NMR CDCl$_3$ ppm 1.23 (s): 12Me; 1.37 (s): 6Me; 2.26 (s): N-(Me)$_2$; 2.73 (s): 6-OMe; 3.67 (m): H$_8$; 3.79 (AB): NCH$_2$Ar; 3.86 (q): H$_2$; 3.99 (m): NO—CH; 7.24–7.32: aromatics.

EXAMPLE 44

3-de[(2,6-dideoxy-3-C-methyl-3-O-methyl-α-L-ribohexopyranosyl)-oxy]-6-O-methyl-3-oxo-erythromycin (E) (R) 9-O-(1-(8-phenyloctyl)-3-piperidinyl)-oxime was obtained using Operating Method 1 and its Mass spectrum: MH$^+$ =874$^+$ NMR CDCl$_3$ ppm 1.25: 12Me; 1.38: 6Me; 2.26: N-(Me)$_2$; 2.56: H$_{10}$; 2.60: <u>CH$_2$</u>Φ; 2.74: 6-OMe; 3.18: H$_2'$; 3.68: H$_8$; 3.85: H$_2$; 4.03: N—OCH; 7.16–7.26: aromatics.

EXAMPLE 45

3-de[(2,6-dideoxy-3-C-methyl-3-O-methyl-α-L-ribohexopyranosyl)-oxy]-6-O-methyl-3-oxo-erythromycin (E) (R) 9-O-(1(3-(4-nitrophenyl)-2(E)-propenyl)-3-piperidinyl)-oxime was obtained using Operating Method 3 and its Mass spectrum: MH$^+$=847$^+$ NMR CDCl$_3$ ppm 1.22: 12Me; 1.37: 6Me; 2.26: N-(Me)$_2$; 2.56: H$_{10}$; 2.73: 6-OMe; 3.05 to 3.20: H$_2'$, H$_4$; 3.67: H$_8$; 3.86: H$_2$; 4.06: N—OCH; 7.5-8.17: —Φ-NO$_2$.

EXAMPLE 46

3-de[(2,6-dideoxy-3-C-methyl-3-O-methyl-α-L-ribohexopyranosyl)-oxy]-6-O-methyl-3-oxo-erythromycin (E) (R) 9-O-(1(3-(methyloctylamino)-propyl)-3-piperidinyl)-oxime was obtained using Operating Method and its Mass spectrum: MH$^+$=869$^+$ NMR CDCl$_3$ ppm 1.27 (s): 12Me; 1.38 (s): 6Me; 2.22 (s): N-Me; 2.26 (s): N-(Me)$_2$; 3.68 (m): H$_8$; 3.86 (q): H$_2$; 4.03 (m): NO—CH; 5.17 (dd): H$_{13}$.

EXAMPLE 47

3-de[(2,6-dideoxy-3-C-methyl-3-O-methyl-α-L-ribohexopyranosyl)-oxy]-6-O-methyl-3-oxo-erythromycin (E) (R) 9 -O-(1(3-((benzyl)-(4-phenyl-1-oxobutyl)-amino)-propyl)-3-piperidinyl)-oxime was obtained using Operating Method and its Mass spectrum: MH$^+$=979$^+$ NMR CDCl$_3$ ppm 2.26 (s) : N-(Me)$_2$; 3.68 (m): H$_8$; 3.98 (m): NO—CH; 4.48-4.6 (AB): NCH$_2$Ar; 5.16 (dd): H$_{13}$; 7.05-7.4: the aromatics.

EXAMPLE 48

3-de[(2,6-dideoxy-3-C-methyl-3-O-methyl-α-L-ribohexopyranosyl)-oxy]-6-O-methyl-3-oxo-erythromycin (E) (R) 9 -O-(1(3-(1,1-biphenyl-4-yl)-2(E)-propenyl)-3-piperidinyl)-oxime was obtained using Operating Method 1 and its Mass spectrum: Mh$^+$=878$^+$ NMR CDCl$_3$ ppm 1.22 (s): 12Me; 1.38 (s): 6Me; 2.25 (s): N-(Me)$_2$; 2.76 (s): 6-OMe; 3.69 (m) : H$_8$; 3.86 (q) : H$_2$; 5.16 (dd) H$_{13}$; 6.29-6.53: ethylenics; 7.3-7.6: aromatics.

EXAMPLE 49

3-de[(2,6-dideoxy-3-C-methyl-3-O-methyl-α-L-ribohexopyranosyl)-oxy]-6-O-methyl-3-oxo-erythromycin (E) (R) 9 -O-(1(3-(methyl-benzyl)-amino)-propel)-3-piperidinyl)-oxime was obtained using Operating Method and its Mass spectrum: MH$^+$=847$^+$ NMR CDCl$_3$ ppm 1.25 (s): 12Me; 1.38 (s): 6Me; 2.18 (s) NMe; 2.25 (s): N-(Me)$_2$; 2.74 (s): 6-OMe; 3.47 (s): CH$_2$Ar; 3.68 (m): H$_8$; 3.86 (q): H$_2$; 5.17: H$_{13}$; 7.24-7.3: aromatics.

EXAMPLE 50

3-de[(2,6-dideoxy-3-C-methyl-3-O-methyl-α-L-ribohexopyranosy)-oxy]-6-O-methyl-3-oxo-erythromycin (E) (R) 9-O-(1-(3-(4-phenyl-1H-imidazol-1-yl)-propyl)-3-piperidinyl)-oxime was obtained using Operating Method 1 and its Mass spectrum: Mh$^+$=870$^+$ NMR CDCl$_3$ ppm 1.23 (s): 12Me; 1.38 (s): 6Me; 2.25 (s): N-(Me)$_2$; 3.68 (m): H$_8$; 3.86 (q): H$_2$; 4.05 (m): NO—CH; 5.14 (dd): H$_{13}$; 7.2-7.49: H imidazole; 7.22-7.36-7.76: the aromatics.

EXAMPLE 51

3-de[(2,6-dideoxy-3-C-methyl-3-O-methyl-α-L-ribohexopyranosyl)-oxy]-6-O-methyl-3-oxo-erythromycin (E) (R) 9-O-(1-(3-(4-phenoxyphenyl)-2(E)-propenyl)-3-piperidinyl)-oxime was obtained using Operating Method 1 and its Mass spectrum: Mh$^+$=895$^+$ NMR CDCl$_3$ ppm 1.22 (s): 12Me; 1.38 (s): 6Me; 2.27 (s): N-(Me)$_2$; 2.74 (s): 6-OMe; 3.69 (m) : H$_8$; 3.86 (q): H$_2$; 4.02 (m): NO—CH; 5.15 (dd): H$_{13}$; 6.15 and 6.46 (J=16Hz): =CH; 6.9 to 7.4: aromatics.

EXAMPLE 52

3-de[(2,6-dideoxy-3-C-methyl-3-O-methyl-α-L-ribohexopyranosyl)-oxy]-6-O-methyl-3-oxo-erythromycin (E) (R) 9-O-(1(3-(4-butoxyphenyl)-propyl)-3-piperidinyl)-oxime was obtained using Operating Method 1 and its Mass spectrum: Mh$^+$=876.7$^+$ NMR CDCl$_3$ ppm 1.23: 12Me; 1.37: 6Me; 2.26: N-(Me)$_2$; 2.30-2.60: H$_{10}$; 2.74: 6-OMe; 3.70: H$_2'$; 3.68: H$_8$; 3.87: H$_2$; 4.05: NO—CH; 3.95: —Φ-O—CH$_2$; 6.85-7.08: -Φ-.

EXAMPLE 53

3-de[(2,6-dideoxy-3-C-methyl-3-O-methyl-α-L-ribohexopyranosyl)-oxy]-6-O-methyl-3-oxo-erythromycin (E) (R) 9 -O-(1(3-((((1,1 '-biphenyl-4-yl)-methyl)-amino)-propyl)-3-piperidinyl)-oxime was obtained using Operating Method and its Mass spectrum: Mh$^+$=909$^+$ NMR CDCl$_3$ ppm 1.23 (s): 12Me; 1.38 (s): 6Me; 2.26 (s): N-(Me)$_2$2.74 (s): 6-OMe; 3.45 (m): H$_8$; 3.83 (s): CH$_2$Ar; 3.86: H$_2$; 4.02 (m): NO—CH; 5.17 (dd): H$_{13}$; 7.3-7.6: aromatics.

EXAMPLE 54

3-de[(2,6-dideoxy-3-C-methyl-3-O-methyl-α-L-ribohexopyranosyl)-oxy]-6-O-methyl-3-oxo-erythromycin (E) (R) 9 -O-(1(3-(dodecylamino)-propyl)-3-piperidinyl)-oxime was obtained using Operating Method and its Mass spectrum: Mh$^+$=911$^+$ NMR CDCl$_3$ ppm 0.96-1.14: CH$_3$—(CH)$_n$; 1.37 (s): 6Me; 2.3 (s): N-(Me)$_2$; 2.76 (s): 6-OMe; 3.68 (m): H$_8$; 3.86 (q): H$_2$; 5.17 (dd): H$_{13}$.

EXAMPLE 55

3-de[(2,6-dideoxy-3-C-methyl-3-O-methyl-α-L-ribohexopyranosyl)-oxy]-6-O-methyl-3-oxo-erythromycin (E) (R) 9-O-(1-(4-(2,4,6-trimethylphenyl)-butyl)-3-piperidinyl)-oxime was obtained using Operating Method 1 and its Mass spectrum: Mh$^+$=860$^+$ NMR CDCl$_3$ ppm 1.22: 12Me; 1.37: 6Me; 2.26: N-(Me)$_2$; 2.56: H$_{10}$; 3.18: H$_2'$; 3.68: H$_8$; 3.86: H$_2$; 4.04: N—OCH; 7.4 to 7.7: -Φ-.

EXAMPLE 56

3-de[(2,6-dideoxy-3-C-methyl-3-O-methyl-α-L-ribohexopyranosyl)-oxy]-6-O-methyl-3-oxo-erythromycin (E) (R) 9-O-(1-(5-phenylpentyl)-3-piperidinyl)-oxime was obtained using Operating Method 1 and its NMR CDCl$_3$ ppm 1.23: 12Me; 1.38: 6Me; 2.26: N-(Me)$_2$; 2.58: H$_{10}$; 2.61: CH$_2$Φ; 2.74: 6-OMe; 3.18: H$_2'$; 3.67: H$_8$; 3.85: H$_2$; 4.04: N—OCH; 7.15 to 7.35: aromatics.

EXAMPLE 57

3-de[(2,6-dideoxy-3-C-methyl-3-O-methyl-α-L-ribohexopyranosyl)-oxy]-6-O-methyl 3-oxo-erythromycin (E) (R) 9-O-(1-(3,7,11-trimethyl 2(E), 6(E), 10-dodecatrienyl)-3-piperidinyl)-oxime was obtained using Operating Method 1 and its Mass spectrum: Mh$^+$=890$^+$ NMR CDCl$_3$ ppm 1.22 (s): 12Me; 1.30 (s): 6Me; 1.6-1.62: vinyl CH$_3$'s; 2.26 (s): N(Me)$_2$; 3.68 (m): H$_8$; 3.86 (q): H$_2$; 4.05 (m): NO—CH; 5.05-5.25: vinyl H's.

EXAMPLE 58

3-de[(2,6-dideoxy-3-C-methyl-3-O-methyl-α-L-ribohexopyranosyl)-oxy]-6-O-methyl-3-oxo-erythromycin (E) (R) 9-O-(1(3-(3,4,5-trimethoxyphenyl)-propyl)-3-piperidinyl)-oxime was obtained using Operating Method 1 and its Mass spectrum: $Mh^+=894^+$ NMR CDCl$_3$ ppm 1.23: 12Me; 1.38: 6Me; 2.26: N-(Me)$_2$; 2.39: H$_{10}$; 2.74: 6-OMe; 3.18: H$_2$'; 3.68: H$_8$; 3.8: H$_2$; 4.05: NO—CH; 6.41: aromatics.

EXAMPLE 59

3-de[(2,6-dideoxy-3-C-methyl-3-O-methyl-α-L-ribohexopyranosyl)-oxy]-6-O-methyl-3-oxo-erythromycin (E) (R) 9 -O-(1(5-((2-methoxyethoxy)-methoxy)-pentyl)-3-piperidinyl)-oxime was obtained using Operating Method 1 and its NMR CDCl$_3$ ppm 1.38 (s): 6Me; 2.26 (s): N-(Me)$_2$; 2.76 (s): 6-OMe; 3.52–3.71: OCH$_2$C-H$_2$O; 3.82 (q): H$_2$; 4.09: NO—CH; 4.72: OCH$_2$O: 5.17 (dd): H$_{13}$.

EXAMPLE 60

3-de[(2,6-dideoxy-3-C-methyl-3-O-methyl-α-L-ribohexopyranosyl)-oxy]-6-O-methyl-3-oxo-erythromycin (E) (R) 9 -O-(1(6-phenylhexyl)-3-piperidinyl)-oxime was obtained using Operating Method 1 and its Mass spectrum: $Mh^+=846^+$ NMR CDCl$_3$ ppm 1.23: 12Me; 1.38: 6Me; 2.26: N-(Me)$_2$2.60: CH$_2$Φ; 2.74: 6-OMe; 3.19: H$_2$'; 3.69: H$_8$; 3.87: Hz; 4.04: N—OCH; 7.10 to 7.30: the aromatics.

EXAMPLE 61

3-de[(2,6-dideoxy-3-C-methyl-3-O-methyl-α-L-ribohexopyranosyl)-oxy]-6-O-methyl-3-oxo-erythromycin (E) (R) 9-O-(1-(6-((4,6-dimethyl-2-pyrimidinyl)-thio)-hexyl)-3-piperidinyl)oxime was obtained using Operating Method 1 and its Mass spectrum: $Mh^+=908^+$ NMR CDCl$_3$ ppm 1.23 (s): 12Me; 1.38 (s): 6Me; 2.26 (s): N-(Me)$_2$; 2.39 (s): aromatic CH$_3$'s; 2.7 (s): 6-OMe; 3.68 (m): H$_8$; 3.86 (q): H$_2$; 4.04: NO—CH; 5.17 (dd): H$_{13}$; 6.67: the aromatics.

EXAMPLE 62

3-de[(2,6-dideoxy-3-C-methyl-3-O-methyl-α-L-ribohexopyranosyl)-oxy]-6-O-methyl-3-oxo-erythromycin (E)(R) 9-O-(1-(5-((4,4,5,5,5-pentafluoropentyl)-sulfonyl)-pentyl)-3-piperidinyl)-oxime was obtained using Operating Method 1 and its NMR CDCl$_3$ ppm 1.23 (S): 12Me; 1.38 (s): 6Me; 2.26 (m): N-(Me)$_2$; 2.76 (s): 6-OMe; 2.97–3.10: CH$_2$SO$_2$; 3.67 (m): H$_8$; 3.87 (q): H$_2$; 4.02: NO—CH; 5.16 (dd): H$_{13}$.

EXAMPLE 63

3-de[(2,6-dideoxy-3-C-methyl-3-O-methyl-y-L-ribohexopyraosyl)-oxy] -6-O-methyl-3-oxo-erythromycin (E) (R) 9-O-(1tetradecyl 3-piperidinyl)-oxime was obtained using Operating Method 1 and its Mass spectrum: $Mh^+=882.8^+$ NMR CDCl$_3$ ppm 1.25: 12Me; 1.38: 6Me; 2.26: N-(Me)$_2$; 2.56: H$_{10}$; 2.74: 6-OMe; 3.19: H$_2$'; 3.68: H$_8$; 3.86: H$_2$; 4.04: NO—CH.

EXAMPLE 64

3-de[(2,6-dideoxy-3-C-methyl-3-O-methyl-α-L-ribohexopyranosyl)-oxy]-6-O-methyl-3-oxo-erythromyc in (R) (E) 9 -O-(1-(4-(1,1'-biphenyl 4-yl)-butyl)-3-piperidinyl)-oxime was obtained using Operating Method 2 and its Mass spectrum: $Mh^+=894^+$ NMR CDCl$_3$ ppm 1.23 (s): 12Me; 1.39 (s): 6Me; 2.66 (t): CH$_2$Ar; 3.68 (m): H$_8$; 3.86 (q): H$_2$; 4.05 (m): NO—CH; 5.17: H$_{13}$; 7.25–7.59: aromatics.

EXAMPLE 65

3-de[(2,6-dideoxy-3-C-methyl-3-O-methyl-α-L-ribohexopyranosyl)-oxy]-6-O-methyl-3-oxo-erythromycin (R) (E) 9-O-(1(3-(4-phenoxyphenyl)-propyl)-3-piperidinyl)-oxime was obtained using Operating Method and its Mass spectrum: $Mh^+=896^+$ NMR CDCl$_3$ ppm 1.22 (s): 12Me; 1.38 (s): 6Me; 2.26 (s): N-(Me)$_2$; 2.6: CH$_2$Ar; 2.76 (s): 6-OMe; 3.86 (q): H$_2$; 4.05 (m): NO—CH; 5.17 (dd): H$_{13}$; 6.85–7.9: aromatics.

EXAMPLE 66

3-[(2,6-dideoxy-3-C-methyl-3-O-methyl-α-L-ribohexopyranosyl)-oxy]-6-O-methyl-3-oxo-erythromycin (R) (E) 9-O-(1-(4-(3-(3,5-dichlorophenoxy)-phenyl)-butyl)-3-piperidinyl)-oxime was obtained using Operating Method 1 and its Mass spectrum: $Mh^+=978^+$ NMR CDCl$_3$ ppm 1.23 (s): 12Me; 1.38 (s): 6Me; 2.26 (s): N-(Me)$_2$; 2.76 (s): 6-OMe; 3.67 (m): H$_8$; 3.86 (q): H$_2$; 4.03 (m): NO—CH; 5.18 (dd): H$_{13}$; 6.85 (d)-7.05 (t)-6.82-7.29-7.03: aromatics.

EXAMPLE 67

3-de[(2,6-dideoxy-3-C-methyl-3-O-methyl-α-L-ribohexopyranosyl)-oxy]-6-O-methyl-3-oxo-erythromycin (R) (E) 9-O-(1-(6-((4-methylphenyl)-thio)-hexyl)-3-piperidinyl)-oxime was obtained using Operating Method 1 and its Mass spectrum: $Mh^+=892^+$ NMR CDCl$_3$ ppm 1.22: 12Me; 1.38: 6Me; 2.26: N-(Me)$_2$; 2.31: CH$_3$—Φ; 2.56: H$_{10}$; 2.74: 6OMe; 2.87: S—CH$_2$; 3.18: H$_2$'; 3.69: H$_8$; 3.86: H$_2$; 4.03: N—OCH$_2$; 7.09 and 7.24: —Φ-S.

EXAMPLE 68

3-de[(2,6-dideoxy-3-C-methyl-3-O-methyl-α-L-ribohexopyranosyl)-oxy]-6-O-methyl-3-oxo-erythromycin (E) (R) 9 -O-(1-(4-(4-butylphenyl)-butyl)-3-piperidinyl)-oxime was obtained using Operating Method 1 and its Mass spectrum: $Mh^+=874.6^+$ NMR CDCl$_3$ ppm 1.23: 12Me; 1.38: 6Me; 2.26: N-(Me)$_2$; 2.58:H$_{10}$ and CH$_2$Φ; 2.74: 6-Ome; 3.19: H$_2$'; 3.68: H$_8$; 3.87: H$_2$; 4.03: NO—CH; 7.08: -Φ-.

EXAMPLE 69

3-de[(2,6-dideoxy-3-C-methyl-3-O-methyl-α-L-ribohexopyranosyl)-oxy]-6-O-methyl-3-oxo-erythromycin (R) (E) 9-O-(1-(6-(4-chlorophenoxy)-hexyl)-3-piperidinyl)-oxime was obtained using Operating Method 1 and its Mass spectrum: $Mh^+=896^+$ NMR CDCl$_3$ ppm 1.24: 12Me; 1.38: 6Me; 2.26: N-(Me)$_2$; 2.56: H$_{10}$; 2.74: 6-OMe; 3.68: H$_8$; 3.86: H$_2$; 4.04: axial =N—O—CH; 6.82: —Φ-Cl.

EXAMPLE 70

3-de[(2,6-dideoxy-3-C-methyl-3-O-methyl-α-L-ribohexopyranosyl)-oxy]-6-O-methyl-3-oxo-erythromycin (E) (R) 9 -O-(1-(3-((4-methylphenyl)-thio)-propyl)-3-piperidinyl)-oxime was obtained using Operating Method 1 and its Mass spectrum: $Mh^+=850^+$ NMR CDCl$_3$ ppm 1.29 (s): 12Me; 1.37 (s): 6Me; 2.28 (s): N-(Me)$_2$; 2.32 (s): CH$_3$Ar; 2.99: CH$_2$—S; 3.67 (m): H$_8$; 3.86 (q): H$_2$; 5.17 (dd): H$_{13}$; 7.09–7.25: aromatics.

EXAMPLE 71

3-de[(2,6-dideoxy-3-C-methyl-3-O-methyl-α-L-ribohexopyranosyl)-oxy]-6-O-methyl-3-oxo-erythromycin (E) (R) 9-O-(1-(4-(4-(1H-pyrrol-1-yl)-phenyl)-butyl)-3-piperidinyl)-oxime was obtained using Operating Method 2 and its Mass spectrum: Mh+ =883+ NMR CDCl3 ppm 1.23 (s): 12Me; 1.39 (s): 6Me; 2.26 (s): N-(Me)2; 2.64: CH2Ar; 2.76 (s): 6-OMe; 3.68 (m): H8; 3.86 (q): H2; 4.04 (m): NO—CH; 5.18 (dd): H13; 6.33–7.07: pyrrole; 7.22–7.31: phenyl.

EXAMPLE 72

3-de[(2,6-dideoxy-3-C-methyl-3-O-methyl-α-L-ribohexopyranosyl)-oxy]-6-O-methyl-3-oxo-erythromycin (E) (R) 9 -O-(1-(4-(5-butyl-2-pyridinyl)-butyl)-3-piperidinyl)-oxime was obtained using Operating Method 2 and its Mass spectrum: Mh+ =875+ NMR CDCl3 ppm 1.23 (s): 12Me; 1.38 (s): 6Me; 2.26 (s): N-(Me)2; 2.57 (t) and 2.76 (t): benzyl CH2; 3.68 (m): H8; 3.86 (q): H2; 5.17 (dd): H13; 7.06–7.4–8.33: pyridine.

EXAMPLE 73

3-de[(2,6-dideoxy-3-C-methyl-3-O-methyl-α-L-ribohexopyranosyl)-oxy]-6-O-methyl-3-oxo-erythromycin (E) (R) 9-O-(1-(3-(phenylmethoxy)-propyl)-3-piperidinyl)-oxime was obtained using Operating Method 1 and its Mass spectrum: Mh+ =832+ NMR CDCl3 ppm 1.23: 12Me; 1.38: 6Me; 2.26: N-(Me)2; 2.56: H10; 2.73: 6-OMe; 3.18: H2'; 3.50: OCH; 3.68: H8; 3.86: H2; 4.03: axial N—O—CH; 4.5: O—CH2Φ; 7.25 to 7.40: aromatics

EXAMPLE 74

3-de[(2,6-dideoxy-3-C-methyl-3-O-methyl-α-L-ribohexopyranosyl)-oxy] -6-O-methyl-3-oxo-erythromycin (E) (R) 9-O-(1-(3-(4-phenylcyclohexyl)-propel)-3-piperidinyl)-oxime was obtained using Operating Method 1 and its Mass spectrum: Mh+ =886+ NMR CDCl3 ppm 1.23: 12Me; 1.38: 6Me; 2.26: N-(Me)2; 2.57: H10; 3.18: H2'; 3.68: H8; 3.86: H2; 4.05: axial N—O—CH; 7.14 to 7.30: aromatics.

EXAMPLE 75

3-de[(2,6-dideoxy-3-C-methyl-3-O-methyl-α-L-ribohexopyranosyl)-oxy]-6-O-methyl-3-oxo-erythromycin (E) (R) 9-O-(1-(4-(4-(4-pyridinyl)-phenyl)-butyl)-3-piperidinyl)-oxime was obtained using Operating Method 2 and its Mass spectrum: Mh+ =895+ NMR CDCl3 ppm 1.23: 12Me; 1.38: 6Me; 2.27: N-(Me)2; 2.58: H10; 2.69: CH2Φ; 2.75: 6-OMe; 3.20: H2'; 3.67: H8; 3.87: H2; 4.06: NOCH; 7.30–7.57: phenyl; 7.51–8.64: pyridine.

EXAMPLE 76

3-de[(2,6-dideoxy-3-C-methyl-3-O-methyl-α-L-ribohexopyranosyl)-oxy]-6-O-methyl-3-oxo-erythromycin (E) (R) 9 -O-(1-(3-(4-methylphenyl)-propyl)-3-piperidinyl)-oxime was obtained using Operating Method 2 and its Mass spectrum: Mh+ =158, 818+ NMR CDCl3 ppm 2.31: CH3Φ; 2.57: CH2Φ; 3.67: H8; 4.04: NO—CH<; 7.08: phenyl.

EXAMPLE 77

3-de[(2,6-dideoxy-3-C-methyl-3-O-methyl-α-L-ribohexopyranosyl)-oxy]-6-O-methyl-3-oxo-erythromycin (E) (R) 9-O-(1-(3-(3-hydroxyphenyl)-propyl)-3-piperidinyl)-oxime was obtained using Operating Method 1 and its Mass spectrum: Mh+ =158, 820+ NMR CDCl3 ppm 2.3 to 2.7: CH2Φ; 3.65: H8; 4.06: NO—CH<; 6.67 (3H)–7.11 (1H): phenyl.

EXAMPLE 78

3-de[(2,6-dideoxy-3-C-methyl-3-O-methyl-α-L-ribohexopyranosyl)-oxy]-6-O-methyl-3-oxo-erythromycin (E) (R) 9-O-(1-(4-(4-hydroxyphenyl)-butyl)-3-piperidinyl)-oxime was obtained using Operating Method 1 and its Mass spectrum: Mh+ =834, 840+ NMR CDCl3 ppm 3.63: H8; 4.00: NO—CH<; 6.80–7.00: phenyl.

EXAMPLE 79

3-de[(2,6-dideoxy-3-C-methyl-3-O-methyl-α-L-ribohexopyranosyl)-oxy]-6-O-methyl-3-oxo-erythromycin (E) (R) 9-O-(1-(3-(4-hydroxyphenyl)-propyl)-3-piperidinyl)-oxime 11,12-cyclic carbonate was obtained using Operating Method 1 and its Mass spectrum: Mh+ =846+ NMR CDCl3 ppm 1.38 (s)–1.55 (s): 6Me; 2.26 (s): N(Me)2; 2.62 (s) 6-OMe; 3.67 (m): H8 (isomer E); 3.83 (q) : H24.09: NO—CH<; 5.05 (dd): H13; 6.76–7.05: hydroxyphenyl.

EXAMPLE 80

3-de[(2,6-dideoxy-3-C-methyl-3-O-methyl-α-L-ribohexopyranosyl)-oxy]-6-O-methyl-3-oxo-erythromycin (E) (R) 9-O-(1(3-(4-quinolinyl)-2(E)-propenyl)-3-piperidinyl)-oxime was obtained using Operating Method 1

EXAMPLE 81

3-de[(2,6-dideoxy-3-C-methyl-3-O-methyl-α-L-ribohexopyranosyl)-oxy]-6-O-methyl-3-oxo-erythromycin (E) (R) 9-O-(1-(3-(4-quinolinyl)-propyl)-3-piperidinyl)-oxime was obtained using Operating Method 1

EXAMPLE 82: of pharmaceutical composition tablets were prepared corresponding to the following formula:

| Product of example 1 | 150 mg |
|---|---|
| Sufficient excipient for | 1 g |

(detail of excipient: starch, talc, magnesium stearate).

EXAMPLE 83: of pharmaceutical composition tablets were prepared corresponding to the following formula:

| Product of example 2 | 150 mg |
|---|---|
| Sufficient excipient for | 1 g |

(detail of excipient: starch, talc, magnesium stearate).

EXAMPLE 84: of pharmaceutical composition tablets were prepared corresponding to the following formula:

| Product of example 4 | 150 mg |
|---|---|
| Sufficient excipient for | 1 g |

(detail of excipient: starch, talc, magnesium stearate).

PHARMACOLOGICAL STUDY OF THE PRODUCTS OF THE INVENTION

A) Activity in vitro

Method of dilutions in liquid medium.

A series of tubes were prepared in which the same amount of sterile nutritive medium was distributed and increasing quantities of the product to be studied are distributed in each tube. Then, each tube was cultured with a bacterial strain and after incubation for twenty-four hours in an oven at 37° C., the growth inhibition was assessed by transillumination which allowed the minimal inhibitory concentrations (M.I.C.) to be determined, expressed in micrograms/ml. The following results were obtained (readings after 24 hours).

| Product of Example 1 | |
|---|---|
| *Staphylococcus aureus* 011UC4 | 0.3 |
| *Staphylococcus aureus* 011HT17 | 0.3 |
| *Staphylococcus aureus* 011G025I | 1.2 |
| *Staphylococcus epidermidis* 012GO11C | 0.3 |
| *Streptococcus pyogenes* group A 02A1UC1 | 0.08 |
| *Streptococcus agalactiae* group B 02B1HT1 | ≦0.02 |
| *Streptococcus sp* group C 02C0CB3 | 0.08 |
| *Streptococcus faecalis* group D 02D2UC1 | 0.08 |
| *Streptococcus faecium* group D 02D3HT1 | 0.08 |
| *Streptococcus sp* group G 02G0Gr5 | 0.04 |
| *Streptococcus mitis* 02MitCB1 | ≦0.02 |
| *Streptococcus agalactiae* group B 02B1SJ1 | 0.3 |
| *Streptococcus sp* group C 02C0CB1 | 0.15 |
| *Streptococcus faecalis* group D 02D2Gr8 | 1.2 |
| *Streptococcus pneumoniae* 032UC1 | 0.08 |
| *Streptococcus pneumoniae* 030SJ1 | 1.2 |
| *Streptococcus pneumoniae* 030SJ5 | 0.3 |
| *Haemophilus influenzae* 351HT3 | 5 |
| *Haemophilus influenzae* 351CB12 | 0.6 |
| *Haemophilus influenzae* 351CA1 | 2.5 |
| Product of Example 2 | |
| *Staphylococcus aureus* 011UC4 | 1.2 |
| *Staphylococcus aureus* 011HT17 | 1.2 |
| *Staphylococcus aureus* 011B18C | 5 |
| *Staphylococcus aureus* 011GR12C | 5 |
| *Staphylococcus aureus* 011G025I | 2.5 |
| *Staphylococcus epidermidis* 012GO11C | 1.2 |
| *Staphylococcus aureus* 011CB20 | 2.5 |
| *Staphylococcus epidermidis* 012GO40 | 2.5 |
| *Streptococcus pyogenes* group A 02A1UC1 | 0.3 |
| *Streptococcus agalactiae* group B 02B1HT1 | 1.2 |
| *Streptococcus sp* group C 02C0CB3 | 1.2 |
| *Streptococcus faecalis* group D 02D2UC1 | 0.3 |
| *Streptococcus faecium* group D 02D3HT1 | 0.3 |
| *Streptococcus sp* group G 02G0GR5 | 1.2 |
| *Streptococcus mitis* 02MitCB1 | 1.2 |
| *Streptococcus pyogenes* group A 02A1SJ1 | 1.2 |
| *Streptococcus agalactiae* group B 02B1SJ1 | 1.2 |
| *Streptococcus sp* group C 02C0CB1 | 0.6 |
| *Streptococcus faecalis* group D 02D2Gr8 | 2.5 |
| *Streptococcus faecalis* group D 02D2DU15 | 2.5 |
| *Streptococcus sp* group G 02G0GR4 | 1.2 |
| *Streptococcus sanguis* 02sgGR10 | 2.5 |
| *Streptococcus mitis* 02MitGR16 | 1.2 |
| *Streptococcus pneumoniae* 032UC1 | 1.2 |
| *Streptococcus pneumoniae* 030SJ1 | 1.2 |
| *Streptococcus pneumoniae* 030SJ5 | 2.5 |
| *Haemophilus influenzae* 351CB12 | 5 |
| Product of Example 4 | |
| *Staphylococcus aureus* 011UC4 | 0.3 |
| *Staphylococcus aureus* 011UC4 + serum | 0.3 |
| *Staphylococcus epidermidis* 012GO11i | 1.2 |
| *Streptococcus pyogenes* group A 02A1UC1 | 0.08 |
| *Streptococcus agalactiae* group B 02B1HT1 | ≦0.02 |
| *Streptococcus faecalis* 02D2UC1 | 0.08 |
| *Streptococcus faecium* group D 02D3HT1 | 0.08 |
| Streptococcus groups G 02G0Gr5 | 0.08 |
| *Streptococcus mitis* 02MitCB1 | ≦0.02 |
| *Streptococcus agalactiae* 02B1SJ1c | 0.3 |
| *Streptococcus sanguis* 02SgGR10i | 0.08 |
| *Streptococcus mitis* 02MitGR16i | 0.08 |
| *Streptococcus pneumoniae* 032UC1 | 0.3 |
| *Streptococcus pneumoniae* 030GR20 | 0.6 |
| *Streptococcus pneumoniae* 030SJ5i | 0.15 |
| *Streptococcus pneumoniae* 030R01 | 0.3 |
| *Streptococcus pneumoniae* 030SJ1c | 2.5 |
| Product of Example 5 | |
| *Staphylococcus aureus* 011UC4 | 2.5 |
| *Staphylococcus aureus* 011G025i | 5 |
| *Staphylococcus aureus* 011CB20c | 5 |
| *Staphylococcus epidermidis* 012GO40c | 5 |

-continued

| *Streptococcus pyogenes* group A 02A1UC1 | 0.3 |
|---|---|
| *Streptococcus agalactiae* group B 02B1HT1 | 0.08 |
| *Streptococcus faecalis* 02D2UC1 | 0.3 |
| *Streptococcus faecium* group D 02D3HT1 | 0.3 |
| Streptococcus group G 02G0Gr5 | 0.6 |
| *Streptococcus mitis* 02MitCB1 | 0.15 |
| *Streptococcus pyogenes* 02A1SJ1c | 2.5 |
| *Streptococcus agalactiae* 02B1SJ1c | 2.5 |
| *Streptococcus faecalis* group D 02D2DU15c | 2.5 |
| *Streptococcus sanguis* 02SgGR10i | 0.3 |
| *Streptococcus mitis* 02MitGR16i | 0.6 |
| *Streptococcus pneumoniae* 032UC1 | 0.3 |
| *Streptococcus pneumoniae* 030GR20 | 0.3 |
| *Streptococcus pneumoniae* 030SJ5i | 1.2 |
| *Streptococcus pneumoniae* 030cr18 | 2.5 |
| *Streptococcus pneumoniae* 030PW23 | 2.5 |
| *Streptococcus pneumoniae* 030R01 | 1.2 |
| Product of Example 21 | |
| *Staphylococcus aureus* 011UC4 | 0.3 |
| *Staphylococcus aureus* 011UC4 + serum | 0.15 |
| *Staphylococcus aureus* 011G025i | 1.2 |
| *Staphylococcus epidermidis* 012GO11i | 0.3 |
| *Streptococcus pyogenes* group A 02A1UC1 | 0.15 |
| *Streptococcus agalactiae* group B 02B1HT1 | 0.04 |
| *Streptococcus faecalis* 02D2UC1 | 0.15 |
| *Streptococcus faecium* group D 02D3HT1 | 0.15 |
| Streptococcus group G 02G0Gr5 | 0.15 |
| *Streptococcus agalactiae* 02B1SJ1c | 0.6 |
| *Streptococcus sanguis* 02SgGR10i | 0.8 |
| *Streptococcus mitis* 02MitGR16i | 0.15 |
| *Streptococcus pneumoniae* 032UC1 | 0.04 |
| *Streptococcus pneumoniae* 030GR20 | 0.08 |
| *Streptococcus pneumoniae* 030SJ5i | 0.3 |
| *Streptococcus pneumoniae* 030cr18 | 0.6 |
| *Streptococcus pneumoniae* 030PW23 | 2.5 |
| *Streptococcus pneumoniae* 030R01 | 0.3 |
| *Haemophilus influenzae* 351HT3 | 5 |
| *Haemophilus influenzae* 351CB12 | 0.6 |
| *Haemophilus influenzae* 351CA1 | 2.5 |
| Product of Example 26 | |
| *Staphylococcus aureus* 011UC4 | 0.3 |
| *Staphylococcus aureus* 011UC4 + serum | 0.6 |
| *Staphylococcus aureus* 011G025i | 2.5 |
| *Staphylococcus epidermidis* 012GO11i | 0.6 |
| *Streptococcus pyogenes* group A 02A1UC1 | 0.08 |
| *Streptococcus agalactiae* group B 02B1HT1 | ≦0.02 |
| *Streptococcus faecalis* 02D2UC1 | 0.08 |
| *Streptococcus faecium* group D 02D3HT1 | 0.08 |
| Streptococcus group G 02G0Gr5 | 0.08 |
| *Streptococcus mitis* 02MitCB1 | 0.04 |
| *Streptococcus agalactiae* 02B1SJ1c | 0.6 |
| *Streptococcus sanguis* 02SgGR10i | 0.3 |
| *Streptococcus pneumoniae* 032UC1 | 0.3 |
| *Streptococcus pneumoniae* 030GR20 | 0.04 |
| *Streptococcus pneumoniae* 030SJ5i | 0.6 |
| *Haemophilus influenzae* 351CB12 | 5 |

Various modifications of the products and methods of the invention may be made without departing from the spirit or scope thereof and it is to be understood that the invention is to be limited only as defined in the appended claims.

What is claimed is:

1. A compound selected from the group consisting of all possible stereoisomeric forms and mixtures thereof of a compound of the formula

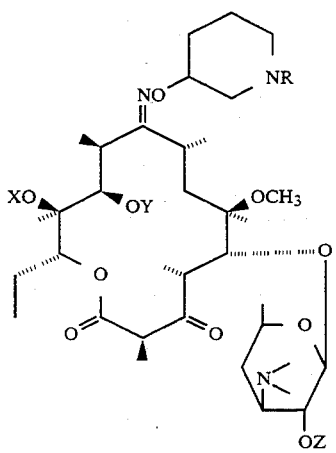

wherein X and Y are hydrogen or together form

R is —(CH$_2$)$_m$—X$_A$, m is an integer from 0 to 20, X$_A$ is selected from the group consisting of alkyl, alkenyl and alkynyl of up to 16 carbon atoms optionally substituted with a halogen, cycloalkyl of 3 to 8 carbon atoms, or

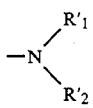

R'$_1$ and R'$_2$ are individually selected from the group consisting of hydrogen and alkyl of 1 to 12 carbon atoms, Z is hydrogen or acyl of an organic carboxylic acid of up to 18 carbon atoms and their non-toxic, pharmaceutically acid addition salts.

2. A compound of claim 1 wherein R is selected from the group consisting of undecyl, dodecyl, and 3-cyclohexyl propyl.

3. A compound of claim 1 wherein R is —(CH$_2$)$_m$—X$_A$ wherein X$_A$ is phenyl optionally substituted as in claim 1 and m is defined as in claim 1.

4. A compound of claim 1 wherein m is an integer from 2 to 6.

5. A compound of claim 1 wherein X$_A$ is dodecylamino.

6. A compound of claim 1 selected from the group consisting of
3-de((2,6-dideoxy-3-C-methyl-3-O-methyl-α-L-ribohexopyranosyl)-oxy-6-O-methyl-3-oxo-erythromycin (R) (E) 9-O-(1-(3-phenylpropyl)-3-piperidinyl)-oxime, 3-de((2,6-dideoxy-3-C-methyl-3-O-methyl-α-L-ribohexopyranosyl)oxy)-6-O-methyl-3-oxo-erythromycin (R) (E)9-O-(1-(dodecyl-3-piperidinyl)-oxime, 3-de [(2,6-dideoxy-3-C-methyl-3-O-methyl-α-L-ribohexopyranosyl)oxy)-6-O-methyl-3-oxo-erythromycin (R) (E) 9-O-(1-(3-(3-methoxyphenyl)-propyl)-3-piperidinyl)-oxime, 3-de[(2,6-dideoxy-3-C-methyl]-6-O-methyl-α-L-ribohexopyranosyl)-oxy)]-6-O-methyl-3-oxo-erythromycin (R) (E) 9-O-(1-(3-(4-triphenylmethoxy)-butyl)-3-piperidinyl)-oxime, 3-de [(2,6-dideoxy-3-C-methyl-3-O-methyl-α-L-ribohexopyranosyl)-oxy)]-6-O-methyl-3-oxo-erythromycin (R) (E) 9-O-(1-(3-(4-trifluoromethyl)-phenyl)-propyl-3-piperidinyl)-oxime, 3-de [(2,6 -dideoxy-3 -C-methyl-3 -O-methyl-α-L-ribohexopyranosyl)-oxy)]-6-O-methyl-3-oxo-erythromycin (R) (E) 9-O-(1-(3-(3,4-difluorophenyl)-propyl-3-piperidinyl)-oxime, 3-de[(2,6-dideoxy-3-C-methyl-3-O-methyl-α-L-ribohexopyranosyl)-oxy)]-6-O-methyl-3-oxo-erythromycin (E) (Z) 9-O-(1-(4-(4-methylphenyl)-butyl)-3-piperidinyl)-oxime, 3-de [(2,6-dideoxy-3-C-methyl-3-O-methyl-α-L-ribohexopyranosyl)-oxy)]-6-O-methyl-3-oxo-erythromycin (E) (R) 9-O-(1-(2-cyclohexylpropyl)-3-piperidinyl)-oxime, 3-de [(2,6-dideoxy-3-C-methyl-3-O-methyl-α-L-ribohexopyranosyl)-oxy)]-6-O-methyl-3-oxo-erythromycin (E) (R) 9-O-(1-(3-(4-hydroxyphenyl)-propyl)-3-piperidinyl)-oxime, 3de[(2,6-dideoxy-3-C-methyl-3-O-methyl-α-L-ribohexopyranosyl)-oxy)]-6-O-methyl-3-oxo-erythromycin (E) (R) 9-O-(1-undecyl-3-piperidinyl)-oxime, 3-de [(2,6-dideoxy-3-C-methyl-3-O-methyl-α-ribohexopyranosyl)oxy)]-6-O-methyl-3-oxo-erythromycin (E) (R) 9-O-(1-(3-(dodecylamino)-propyl)-3-piperidinyl)-oxime, 3-de[(2,6-dideoxy-3-C-methyl -3-O-methyl-α-L-ribohexopyranosyl)-oxy)]-6-O-methyl-3-oxo-erythromycin-9-O-(1-(4-(1,1'-biphenyl-4-yl)-butyl)-3-piperidinyl)-oxime, 3-de[(2,6-dideoxy-3-C-methyl-3-O-methyl-α-L-ribohexopyranosyl)-oxy)]-6-O-methyl-3-oxo-erythromycin-(R) (E) 9-O-(1-(3-(4-phenoxyphenyl)-propyl)-3-piperidinyl)-oxime, 3-de[(2,6-dideoxy-3-C-methyl-3-O-methyl-α-L-ribohexopyranosyl)-oxy)]-6-O-methyl-3-oxo-erythromycin-(R)9-O-(1-(4-(3-(3,5-dichlorophenoxy)-phenyl)-butyl)-3-piperidinyl)-oxime and their non-toxic, pharmaceutically acceptable acid addition salts.

7. A novel antibiotic composition comprising an antibiotically effective amount of at least one compound of claim 1 and an inert pharmaceutical carrier.

8. A method of combatting bacterial infections in warm-blooded animals comprising administering to warm-blooded animals an antibacterically effective amount of at least one compound of claim 1.

9. The method of claim 8 wherein X and Y are hydrogen.

10. The method of claim 8 wherein Z is hydrogen.

* * * * *